United States Patent

Reiner et al.

Patent Number: 5,255,027
Date of Patent: Oct. 19, 1993

[54] EYE TESTING DEVICE

[75] Inventors: Josef Reiner, Cologne; Rainer Kirchhübel, Asslar, both of Fed. Rep. of Germany

[73] Assignee: Oculus Optikgeraete GmbH, Wetzlar, Fed. Rep. of Germany

[21] Appl. No.: 761,324

[22] Filed: Sep. 17, 1991

[30] Foreign Application Priority Data

Dec. 22, 1990 [DE] Fed. Rep. of Germany ... 9017409[U]

[51] Int. Cl.$^5$ ............................................. A61B 3/02
[52] U.S. Cl. ..................................... 351/211; 351/237; 351/239; 351/243
[58] Field of Search ............... 351/211, 239, 240, 241, 351/242, 243, 237; 359/364

[56] References Cited

U.S. PATENT DOCUMENTS 4,299,455 11/1981 Aoki et al. .
4,437,737 3/1984 Rasmussen ........................... 351/237
4,714,320 12/1987 Banbury ............................... 359/364

FOREIGN PATENT DOCUMENTS 0237687 9/1987 European Pat. Off. .
2543903 4/1977 Fed. Rep. of Germany .

Primary Examiner—Rodney B. Bovernick
Assistant Examiner—Hung Xuan Dang
Attorney, Agent, or Firm—Flynn, Thiel, Boutell & Tanis

[57] ABSTRACT

A vision-testing apparatus includes a concave mirror and at least one test object (2) which can be changed in position and is arranged between the concave mirror (1) and its focal point (f) in a first optic path (W1). In order to be able to carry out different vision tests with an apparatus which is simple in design and compact in manufacture, it is provided that the eye (7) of a person being tested is arranged at a focal point (F) of the concave mirror (1) and that between the concave mirror (1) and the test object (2) there is arranged a first partially translucent dividing mirror (3) to form a second optic path (W2) from the concave mirror (1) to the eye (7) of the person being tested.

12 Claims, 3 Drawing Sheets

EYE TESTING DEVICE

FIELD OF THE INVENTION

The invention relates to a vision-testing apparatus having a concave mirror and at least one test object which can be changed in position and is arranged between the concave mirror and its focal point in a first optic path.

BACKGROUND OF THE INVENTION

The closest known state of the art is German Patent No. 24 08 414, which discloses an apparatus for testing the stereoscopic vision. A similar vision-testing apparatus is also disclosed in the "Zentralblatt fuer Arbeitsmedizin, Arbeitsschutz, Prophylaxe und Ergonomie"-(Industrial Medicine, Industrial Safety, Prophylaxis and Ergonomy"), Volume 30 (1980), Pages 110 to 113. This vision-testing apparatus has a concave mirror, at a focal point of which is a test object. A semi-translucent dividing mirror is arranged in the beam path between the test object and the concave mirror, onto which semi-translucent mirror looks the eye of the person tested. This vision-testing apparatus is supposed to enable viewing of vision objects in free space. Through suitable use of the apparatus it is possible to view a test object in free space at any desired distance from infinity to a near point given by the focal distance of the concave mirror. Relatively natural viewing conditions result hereby with respect to the accommodation and convergence for the visual distance of the person tested from infinity to a short distance of approximately five centimeters. Only a single test object is thereby used, the virtual image of which can be projected at any desired distance. The adjustment to various distances is thereby done by moving the test object relative to the combination of partly translucent mirror and concave mirror. The significant disadvantage resulting from this is that both the concave mirror and also the dividing mirror are arranged directly in the vicinity of the eyes of the person tested. Thus, the test object is viewed under the same optic conditions which exist when a magnifying glass is arranged directly in front of the eye of the person tested and when the viewed object is moved relative to the magnifying glass in order to illustrate different optic distances. The individual visual signals appear thereby, depending on the adjusted distance, at different angles. Thus, different resolving power values result with the adjustment of the same visual signals. The larger disclosed visual signals can be more easily recognized by the person tested and simulate a better resolving power. This adulterates in a nonrecheckable manner the testing of the nearsightedness of the person tested.

German Patent No. 32 41 958 discloses an apparatus for carrying out vision tests in which two different optic paths exist, which can be utilized on one hand to test nearsightedness and on the other hand to test farsightedness. When testing the near vision, the optic path does not have a focusing mechanism. The disadvantage of this apparatus is that it must be of a relatively large construction and requires a considerable mechanical input. Furthermore, it is not guaranteed that the viewing direction of the person tested is adjusted exactly to the desired viewing angle, so that the possibility of incorrect tests exists.

Vision-testing devices of the above-mentioned type are utilized to quickly examine the visual functions of the eyes of a person tested. Measurements can be made of the binocular and monocular resolving power of the eye, of the heterophory, of the stereoscopic vision, and of the color vision. Furthermore, such vision-testing devices are also advantageous for testing nearsightedness, hyperopia or presbyopia.

The known vision-testing devices are mostly derived from a simple stereoscope in which the person tested looks through two collective lenses arranged at a fixed distance from one another. The person tested can see test figures or other objects which are arranged in duplicate, each in the focal plane of the lenses. The test images of the test figures, which must be identical, are in this manner optically at infinity so that the pair of eyes of the person tested can merge the two images into one unit. From the fixed arrangement of the two collective lenses result theoretically the same optic viewing relationships, but through the aberation of the lenses, interferences in the binocular vision can occur. A further disadvantage of these known arrangements is that the person tested looks into a dark box, in which the brightly illuminated test figures or test objects are arranged. These are optically reproduced to infinity, but the person tested has, due to the arrangement of the test object inside the box, always the impression of closeness which adulterates the recognition by the person tested. In other words, because the box itself is small, the person looking into it expects to see a test object located close to his or her eyes rather than a test object located (due to optics) at infinity, and therefore when both eyes are being used the person will have a mental tendency to automatically move his or her eyes to the "cross-eyed" state which is normally used to view a close object and which involves highly convergent lines of vision from the respective eyes. This tendency is referred to as pyschical convergence or mental convergence. This too can cause interferences in the monocular or binocular vision, which are expressed by blurred images or double images. A further disadvantage is that, with this type of testing of the resolving power with test objects having optically the same size, different results are obtained in comparison with an ophtalmologic testing of the resolving power at a five or six meter distance.

In addition to the psychical convergence, which is caused by the above-mentioned interferences in the test reading, the instrument nearsightedness plays a role in such viewing devices and causes blurred vision when viewing figures optically shown in infinity. The closeness of the test object is simulated in such devices by inserting additional lenses and prisms between the fixed viewing lenses and the test object. This stimulates the pair of eyes to accommodate and converge, which again results in new sources for error. Due to the limited dimensions of the testing apparatus, only a specific number of such additional lenses and prisms can be used, so that the number of testing distances to be adjusted is seriously limited.

A basic purpose of the invention is to provide a vision-testing apparatus of the above-mentioned type, which with a simple design and with simple reliable operation produces a plurality of vision-testing possibilities, and with a compact design enables a person to be tested with a constant viewing angle.

SUMMARY OF THE INVENTION

This purpose is attained according to the invention by providing, in a device of the above-mentioned type, an arrangement locating the eye of the person tested at the focal point of a concave mirror and by providing a first, partly translucent dividing mirror between the concave mirror and the test object so as to form a second optic path from the concave mirror to the eye of the person tested.

The vision-testing apparatus of the invention has a number of significant advantages. Since according to the invention the eye of the person tested is at the focal point of the concave mirror, a telecentric beam path results. When test objects of the same size are arranged at different distances from the concave mirror within the simple focal distance, then the viewer receives different viewing distances with a natural accommodation and convergence adjustment. The test objects and visual signals appear always at the same angle and thus result in the same resolving power value independent of the focusing distance. The focusing distance ranges from infinity to a close value, which corresponds approximately with the focal distance of the concave mirror. The optical advantages achieved through this are realized in a very compact apparatus, which for example can be used without any difficulties also in medical practices.

A particularly advantageous further development of the invention provides a second, partly translucent dividing mirror in the optic path between the eye of the person tested and the concave mirror. This mirror is preferably inclined at approximately 45° with respect to the vision axis in the main viewing direction, with the optic arrangement which includes the concave mirror and the first dividing mirror being arranged under the second dividing mirror, which enables free viewing. In addition to the very compact design which results from this arrangement, the free view in the horizontal direction of the person tested is not affected. A further advantage of this arrangement is that the movement of the test object can occur in a horizontal direction, from which results significant mechanical advantages.

By suitably dimensioning the concave mirror, it is possible to arrange a further dividing mirror below the position of the previously provided dividing mirror and in front of the eyes of the person tested. This arrangement of the second dividing mirror makes it possible to view the image of the test object, which has come closer, in a downward viewing direction without changing the position of the head of the person tested. Thus, it is possible when testing persons who use a visual aid such as glasses to test different areas of the visual aid, for example a near vision area in a slide view glass. It is particularly advantageous when the second dividing mirror is pivotal in order to change the viewing angle of the person tested, so that by means of only one second dividing mirror both a nearsightedness testing and also a farsightedness testing is possible.

Through the continuous adjustment of the test object from infinity to a very short distance, it is possible to satisfactorily determine a nearsightedness of the person tested in the range from zero to the reciprocal value of the short distance. By using supplemental glasses, a hyperopia can also be detected.

The various test objects can, in the arrangement of the invention, be mounted on a cylinder surface. This has the advantage that a plurality of rectangular test fields can be arranged side-by-side without any loss of space. In contrast, if rectangular test fields are provided on a circular plate, space is always lost, and the number of test fields is limited. Also, the new arrangement has the advantage that the needed light source can be placed within the cylindrical test ring. An influence of the test fields due to heat generation by the light source can easily be avoided through a suitable design.

In order to darken the outer field brightness it is advantageous when the second dividing mirror is associated with an optic light filter. Lastly, it is advisable in order to avoid errors in operation that monocular shutters be used which can each be pivoted automatically into the second optic path when a monocular test program is chosen, and that furthermore a red/green filter is provided which is pivoted automatically into the second optic path when a binocular test according to the anaglyphic method is chosen. In this manner it is assured that, during monocular tests, a cover for the eye not in use swings automatically in front of the eye so that only the vision path to be examined is unobstructed. Through the automatic swinging in of the shutters and also of the red/green filters, it is no longer possible for confusion to occur. Thus, it can no longer happen that, during color tests, a color blind person tested is determined to be capable of seeing colors.

Another dividing method in which strips, masks or the like are directly swung to a position in front of the concave mirror is permitted by the binocular testing with a light background and black symbols or vice versa. Also monocular testing under binocular conditions can be done with this mask design, namely both vision channels are in use but optotypes are offered in only one vision channel.

The vision-testing apparatus of the invention is very compact and small in size so that it can be transported easily. It is thereby advisable to use a concave mirror with a focal distance, which is as short as possible. In order to avoid defects of image aberration, for example image-field curvatures, a suitably dimensioned plus lens is advantageously placed directly in front of the test plane so that such image-field curvature aberrations can be compensated for.

According to the invention, the possibility exists to arrange the test objects on a cylinder surface. This design has the special advantage that a plurality of rectangular test fields can be arranged side-by-side without a loss of space. When the rectangular test fields, as is the case in the state of the art, are provided on a circular plate, then there is a loss of space and the number of test fields is limited. The inventive arrangement of the test objects on a cylinder surface also has the significant advantage that a light source can be arranged within the cylindrical test ring, with the test fields not being affected by heat generated by the light source.

BRIEF DESCRIPTION OF THE DRAWINGS

The invention will be described hereinafter with reference to exemplary embodiments shown in the drawings, in which.

DETAILED DESCRIPTION

Figure 1:
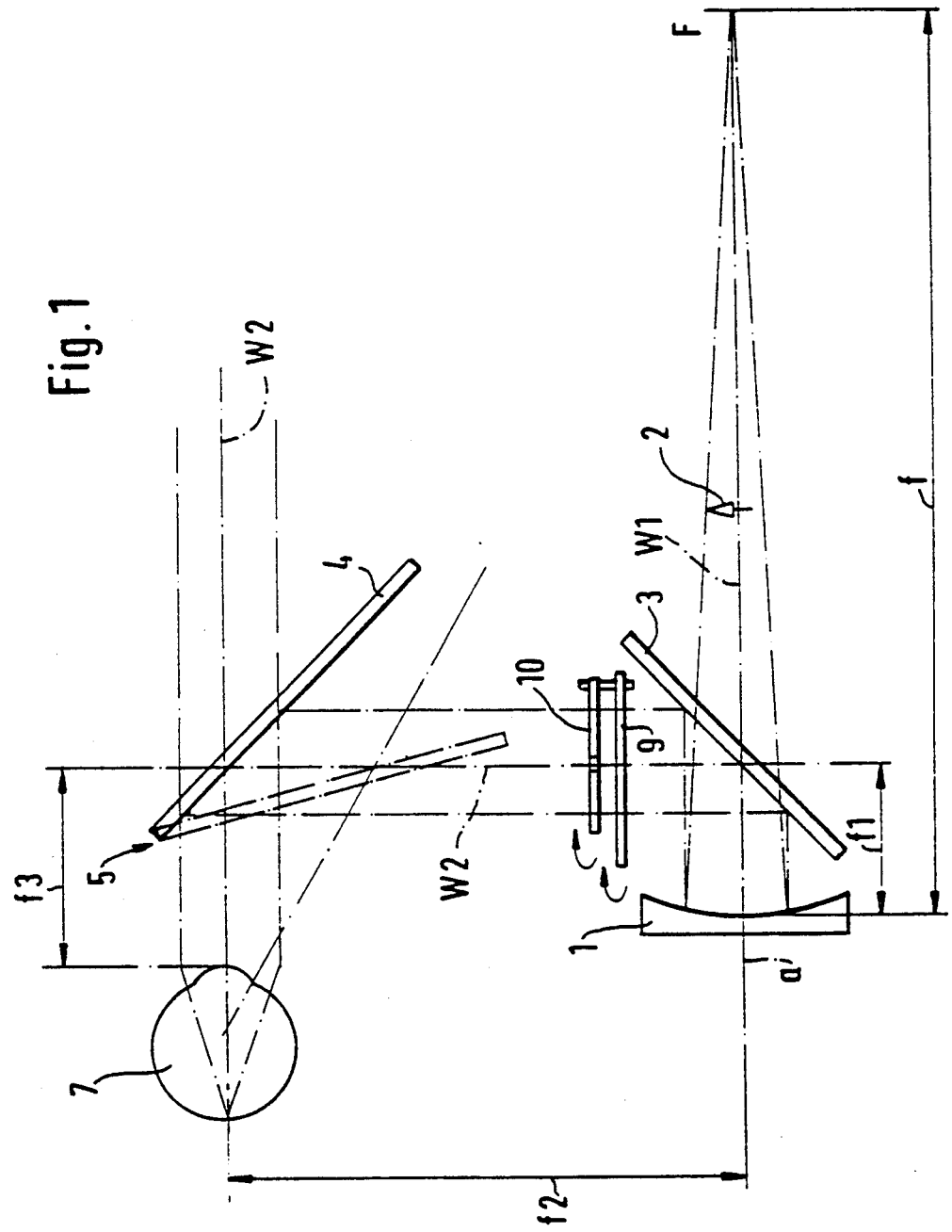
FIG. 1 is a diagrammatic side view of a vision-testing apparatus which embodies the invention and is designed for testing the farsightedness of a person tested.
Figure 2:
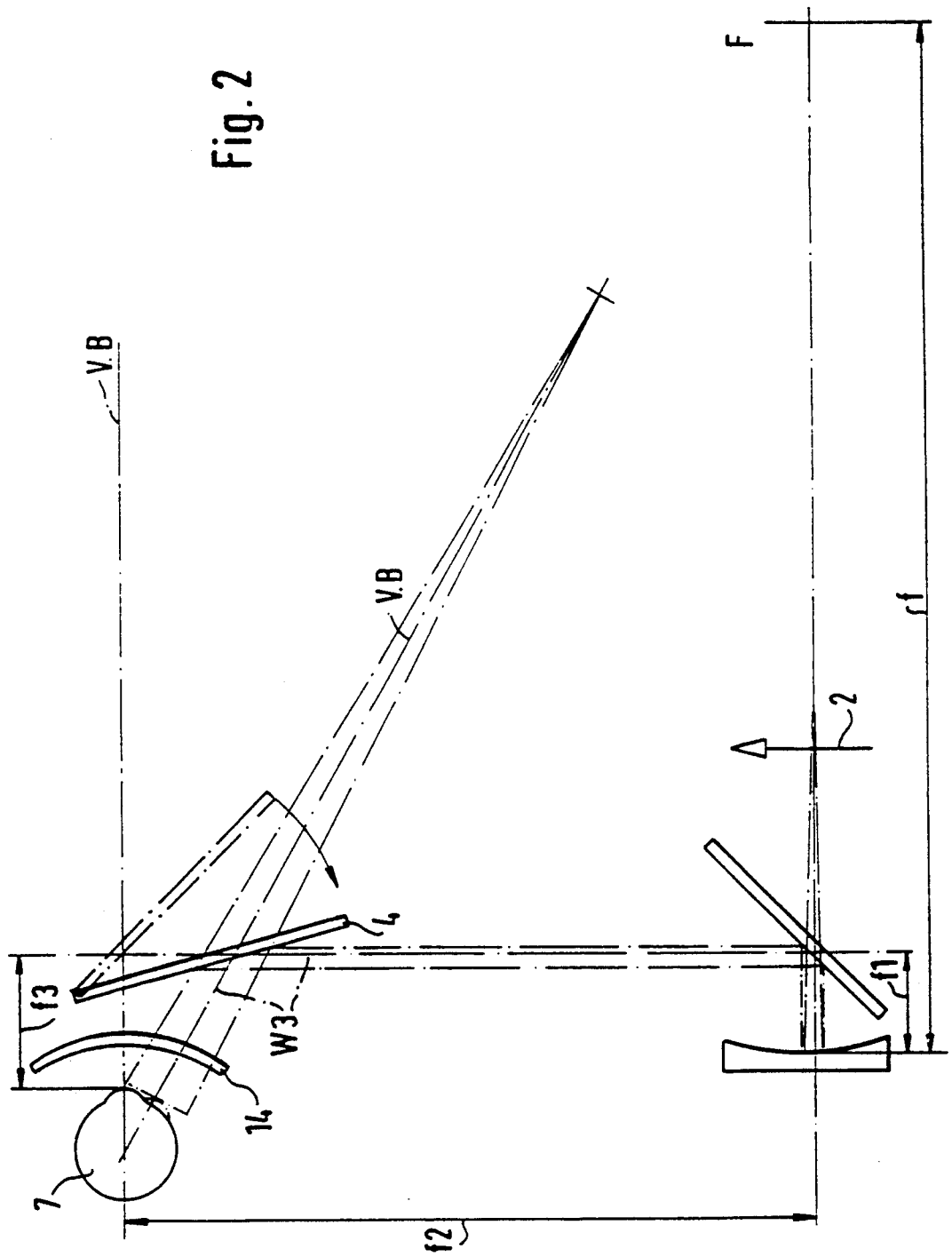
FIG. 2 is a diagrammatic side view of the arrangement illustrated in FIG. 1 during the testing of the nearsightedness of the person tested.

FIGS. 1 and 2 illustrate an exemplary embodiment of the inventive vision-testing apparatus, in which a concave mirror 1 is arranged so that it defines a first, horizontal optic path W1. The letter F identifies the focal point of the concave mirror 1, the focal distance being in the usual manner illustrated with the letter f, and the optic axis of the concave mirror being identified with the letter a. An illuminated test object 2, which is designed for example in the form of an optotype for its realistic illustration, is provided within the focal distance f of the concave mirror 1. A non-illustrated supplementary lens, or rather a combination of lenses, can be arranged directly in front of the test object 2 in order to compensate for defects of the image-field curvature and other defects of image aberration.

The test object 2 can be moved within the focal distance f along the optic path W1.

A nonpivotal, semi-translucent, flat first dividing mirror 3 is arranged at a fixed distance f1 along the optic axis from the concave mirror 1 and is arranged at an angle of 45° to the optic axis a such that some of the light beams reflected by the concave mirror 1 are deflected vertically upwardly, where they hit a second, also semi-translucent flat dividing mirror 4. The second dividing mirror 4 is pivotal about a fulcrum 5, as shown in FIGS. 1 and 2. One position of the second dividing mirror 4 is illustrated in full lines in the figure, while the other possible position is illustrated in dashed lines.

The second dividing mirror 4 can have an optic light filter (not illustrated) in order to darken the outer-field brightness.

FIG. 1 illustrates the second dividing mirror 4 in a position in which it is arranged at 45° to the optic axis a so that the light beams coming from the first dividing mirror 3 are deflected to the horizontal direction and can be guided to one eye 7 of a person being tested. A second optic path W2 is created in this manner, which path includes two parallel horizontal sections and one vertical section. FIG. 1, which depicts the vision-testing apparatus for testing farsightedness, shows the individual sections of the optic path W2 and marks the length of the optic path W2 with the partial focal distances f1, f2, f3. The sum of the partial focal distances f1, f2 and f3 equals the focal distance f of the concave mirror 1.

The eye of the person tested thus always sees in a horizontal viewing direction a sharp (virtual) image of the test object 2 against the background of the surrounding space, so that with a continuous adjustment of the test object 2 from the infinite to a very short distance a satisfactory determination of nearsightedness in a range from zero to the reciprocal value of the short distance is possible.

Farsightedness can also be determined. Supplemental glasses not illustrated in FIG. 1 are to be used here.

Furthermore, FIG. 1 illustrates a shutter 9 and a red/green filter 10, which can be selectively introduced into the beam path of the second optic path W2. The red/green filter 10 is used to determine the capability of the person tested to recognize color, while the shutter 9 is designed so that the beam path to one of the two eyes of the person tested can be obstructed in order to examine the stereoscopic vision effect, and to allow other testing possibilities.

Figure 3:
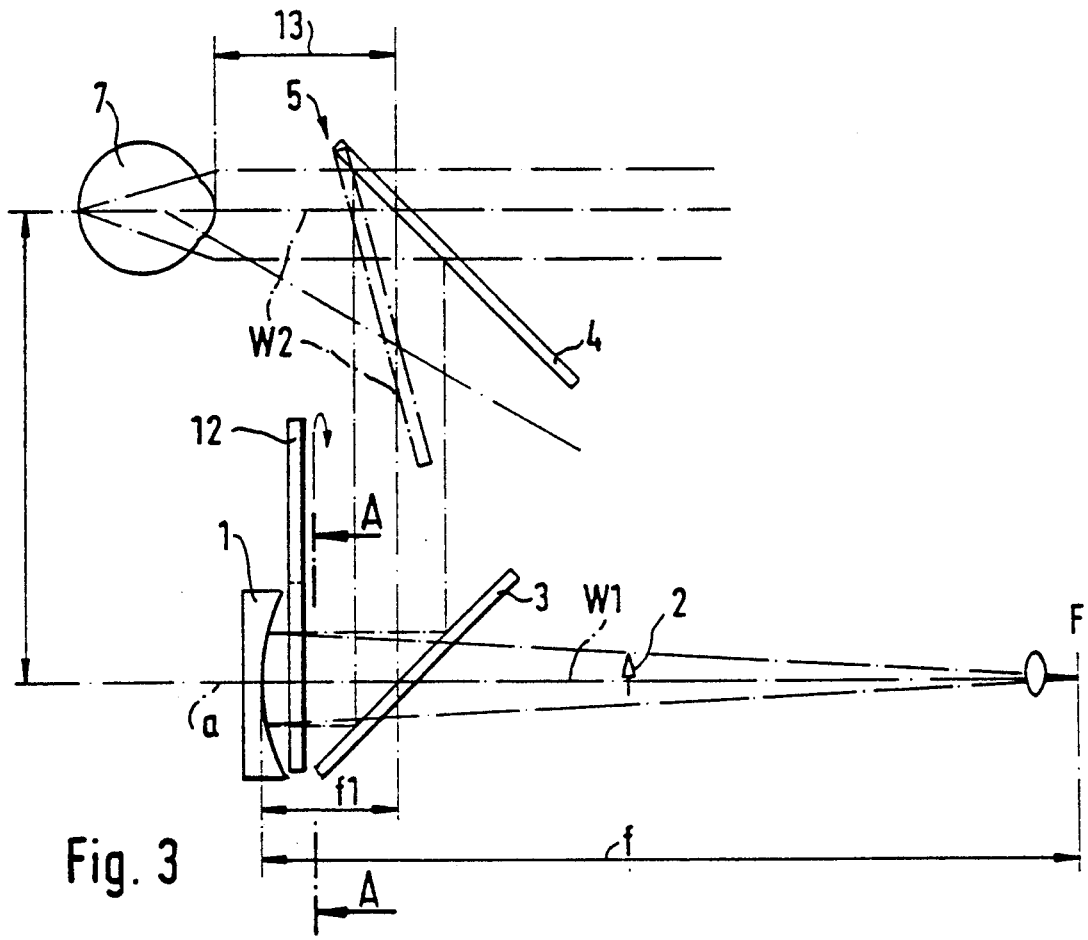
FIG. 3 is a diagrammatic side view which illustrates a further embodiment of the vision-testing apparatus.
Figure 3A:
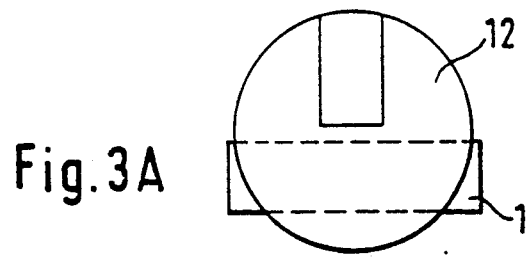
FIGS. 3A and 3B are two sectional views each taken along the line A—A of FIG. 3 and showing different operational positions.
Figure 3B:
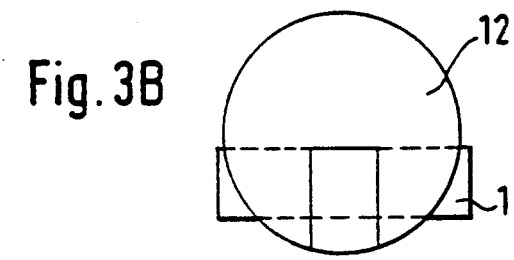

A man skilled in this art will understand that FIGS. 1 to 3 each illustrate only the beam path for one eye of the person tested, while the vision-testing apparatus is of course designed for testing both eyes of the person tested.

The second dividing mirror 4 in the exemplary embodiment is illustrated in FIG. 2 in its lower position so that a third optic path W3 results. When the person tested looks through the lower area of a two-strength vision aid (glasses), an inclination of the optic axis of the eye 7 results caused by said near-vision area of the eye glass 14 as is shown in FIG. 2. Thus, without any further changes in the vision-testing apparatus, it is possible to examine nearsightedness.

The exemplary embodiment illustrated in FIG. 3 provides in addition a correcting lens in order to compensate for defects of image aberration during the use of a short focal distance concave mirror.

As an alternative to the red/green filter 10, FIG. 3 illustrates a mask wheel 12 with which, depending on the mask design, testing can take place monocularly under binocular conditions and with the help of which all binocular tests can be offered.

The invention is not limited to the illustrated exemplary embodiments, because many possibilities for modification are possible within the scope of the invention for a man skilled in the art.

The embodiments of the invention in which an exclusive property or privilege is claimed are defined as follows:

1. A vision-testing apparatus comprising: a concave mirror, a test object arranged between the concave mirror and a focal point on a first optical path of the mirror, wherein between the concave mirror and the test object there is arranged a first, partially translucent dividing mirror to form a second optical path from the concave mirror to the eye of a person tested, and wherein a second, partially translucent dividing mirror is arranged in the second optical path, the eye of the person tested being arranged at a location on the second optical path which is a reflection of the focal point on the first optical path.

2. A vision-testing apparatus according to claim 1, wherein the second dividing mirror is pivotal to change the viewing angle of the eye of the person tested.

3. A vision-testing apparatus according to claim 2, wherein the dividing mirrors are each inclined with respect to the beam path so that the portion of the second optical path which enters the eye of the person tested is parallel to the first optical path lying along the optic axis of the concave mirror.

4. A vision-testing apparatus according to claim 1, wherein the portion of the second optical path which enters the eyes of the person tested and the first optical path each extend horizontally.

5. A vision-testing apparatus according to claim 2, wherein the second dividing mirror is supported in the second optical path for movement to at least two pivot positions, with a visional aid arranged in the viewing direction of the person tested, wherein the aid is arranged to be looked through at least in a near-vision portion and a far-vision portion.

6. A vision-testing apparatus according to claim 1, wherein the second dividing mirror has an optic light filter.

7. A vision-testing apparatus according to claim 1, including a shutter supported for movement between two positions in which the shutter is respectively disposed in and spaced from the second optical path.

8. A vision-testing apparatus according to claim 1, wherein the vision-testing apparatus has a respective optical path for each eye of the person tested.

9. A vision-testing apparatus according to claim 1, including a red/green filter supported for movement between two positions in which the filter is respectively disposed in and spaced from the second optical path.

10. A vision-testing apparatus according to claim 1, wherein a plus lens correcting device is placable in front of the test object.

11. A vision-testing apparatus comprising: a concave mirror, a test object arranged between the concave mirror and a focal point on a first optical path of the mirror, wherein between the concave mirror and the test object there is arranged a first, partially translucent dividing mirror to form a second optical path from the concave mirror to the eye of a person tested, the eye of the person tested being arranged at a location on the second optical path which is a reflection of the focal point on the first optical path, wherein the vision-testing apparatus has a respective optical path for each eye of the person tested, and wherein between the concave mirror and the test object there is a mask object which permits only the right half of the test object to be viewed by the right eye and the left half of the test object to be viewed by the left eye.

12. A vision-testing apparatus according to claim 11, wherein the mask object permits only individual optotypes, rows, or lines to be viewed by each eye or by both eyes.

* * * * *